US007316926B2

(12) United States Patent
Iizasa et al.

(10) Patent No.: US 7,316,926 B2
(45) Date of Patent: Jan. 8, 2008

(54) IMMORTALIZED VASCULAR ADVENTITAL CELL LINE

(75) Inventors: Hisashi Iizasa, Tokyo (JP); Kenji Hattori, Kaisei-machi (JP); Emi Nakashima, Tokyo (JP); Tetsuya Terasaki, Sendai (JP); Masuo Obinata, Sendai (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 572 days.

(21) Appl. No.: 10/204,087

(22) PCT Filed: Feb. 14, 2001

(86) PCT No.: PCT/JP01/01016

§ 371 (c)(1),
(2), (4) Date: Aug. 16, 2002

(87) PCT Pub. No.: WO01/60984

PCT Pub. Date: Aug. 23, 2001

(65) Prior Publication Data

US 2003/0175953 A1  Sep. 18, 2003

(30) Foreign Application Priority Data

Feb. 16, 2000 (JP) .............................. 2000-037827

(51) Int. Cl.
C12N 5/06 (2006.01)
C12N 15/00 (2006.01)
C12N 5/00 (2006.01)

(52) U.S. Cl. ...................... 435/353; 435/455; 435/375; 435/378

(58) Field of Classification Search ..................... None
See application file for complete search history.

(56) References Cited

U.S. PATENT DOCUMENTS 6,825,394 B1 * 11/2004 Rudland et al. .............. 800/14
2002/0045254 A1  4/2002 Hosoya et al. .............. 435/325

FOREIGN PATENT DOCUMENTS

| JP | 05-292958 | | 11/1993 |
| JP | 11-056380 | | 12/1999 |
| WO | WO 91/13150 | * | 8/1991 |
| WO | WO 92/17569 | | 10/1992 |
| WO | WO 97/39117 | | 10/1997 |
| WO | WO 00/20599 | | 4/2000 |

OTHER PUBLICATIONS

Richards SJ, NeuroReport, 1999, 10:i.*
Jat et al., Proc. Natl. Acad. Sci. USA, 1991, 88: 5096-5100.*
Hopfer et al., Am. J. Physiol., 1996, 270: c1-c11.*
Stacey et al., Cell Biol. Toxicol., 2001, 17:231-246, Review.*
Noble et al., Transgenic Research, 1995, 4: 215-225.*
Sanders et al., J. Appl. Physiol., 2000, 88: 1119-1126.*
Maga et al., Review, Transgenic Res., 2003, 12: 485-496, Abstract, Medline PMID 12885169.*
Charreau et al., Review, Transgenic Res., 1996, 5: 223-234, Abstract, Medline PMID 8755162.*
Hosoya et al., AAPS Pharmasci, 2000, 2: 1-11.*
Doherty et al., J. Bone Miner. Res., 1998, 13: 828-838.*
Gerhardt et al., Review, Cell Tissue Res., 2003, 314: 15-23.*
Capetandes et al., Invest. Ophtalmol. Vis. Sci., 1990, 31: 1738-1744.*
Lindahl et al., Science, 1997, 277: 242-245.*
Suri et al., Cell, 1966, 87: 1171-1180.*
Buzney et al., Invest Ophtalmol Vis Sci, 1983, 24: 470-480.*
Yoskikazu Aojika et al., "Regulating factors in lumen formation," Strides of Medicine—Journal of Clinical and Experimental Medicine (Igaku no Ayumi), vol. 191, No. 5, 1999, pp. 315-319.
English translation of Form PCT/IB/338 and Form PCT/IPEA/409 (International Preliminary Examination Report) for PCT/JP01/01016, mailed Aug. 6, 2002, by the International Bureau of WIPO.
J. C. Challier et al., "Mixed Culture Of Pericytes And Endothelial Cells From Fetal Microvessels Of The Human Plasenta," *Cellular and Molecular Biology*, 41(2):233-241, 1995.
K. K. Hirschi et al., "Pericytes in the Microvasculature," *Cardiovascular Research*, 32:687-698, 1996.
A. M. Spence, M.D. et al., "Cerebellar Capillary Hemangioblastoma: Its Histogenesis Studied By Organ Culture and Electron Microscopy," *Cancer*, 35:326-341, 1975.
J. J. Weiter, M.D. et al., "The Clinical and Morphologic Characteristics of Kaposi's Sarcoma of the Conjunctiva," *Am. J. Ophthalm.*, 89:546-552, 1980.
A. Capetandes, et al.,*Simplified Methods for Consistent and Selective Culture of Bovine Retinal Endothelial Cells and Pericytes*, Investigative Ophthalmology & Visual Science, vol. 31, No. 9, pp. 1738-1744, Sep. 1990.
N. Ichikawa, et al., *Isolation and Primary Culture of Rat Cerebral Microvascular Endothelial Cells for Studying Drug Transport in vitro*, Journal of Pharmacological and Toxicological Methods, vol. 36, pp. 45-52, 1996.
Y. K. Kwon, *Expression of Brain-derived Neurotrophic Factor mRNA Stimulated by Basic Fibroblast Growth Factor and Platelet-derived Growth Factor in Rat Hippocampal Cell Line*, Mol. Cells, vol. 7, No. 3, pp. 320-325, 1997.

(Continued)

*Primary Examiner*—Joseph Woitach
*Assistant Examiner*—Ileana Popa
(74) *Attorney, Agent, or Firm*—Morgan & Finnegan L.L.P.

(57) ABSTRACT

To provide an immortalized capillary pericyte line which maintains the original function/property of the cell line-deriving tissue, its establishment method, and the screening method for useful substance using the immortalized capillary pericyte line. Cerebral tissue of a transgenic rat carrying the large T antigen gene of SV40 thermo-sensitive mutant line tsA58 is homogenized and the resultant brain capillaries are treated with protease, thus obtained brain capillary cells are subcultured to establish an immortalized cell that expresses SV40 thermo-sensitive large T antigen, PDGF receptor β, and Angiopoietin-1. In addition, the immortalized vascular pericyte line has ability to deposit calcium on matrix by dense culture.

5 Claims, No Drawings

OTHER PUBLICATIONS

D. Lechardeur, et al., *Induction of Blood-Brain Barrier Differentiation in a Rat Brain-Derived Endothelial Cell Line*, Experimental Cell Research, vol. 220, pp. 161-170, 1995.

M. Noble, et al., *The H-2K$^b$tsA58 transgenic mouse: a new tool for the rapid generation of novel cell lines*, Transgenic Research, vol. 4, pp. 215-225, 1995.

M. Obinata, *Conditionally immortalized cell lines with differentiated functions established from temperature-sensitive T-antigen transgenic mice*, Genes to Cells, vol. 2, pp. 235-244, 1997.

T. Ohno, et al., *A novel Vero cell line for use as a mammalian host-vector system in serum-free medium*, Cytotechnology, vol. 7, pp. 165-172, 1991.

Y. Toyoda, et al., *Fertilization of Rat Eggs In Vitro By Epididymal Spermatozoa and the Development of Eggs Following Transfer*, J. Reprod. Fert., vol. 36, pp. 9-22, 1974.

Yodosha, *Bunshi-seibutsugakuteki approach niyoru gann-kennkyu protocol*, Jikken-Igaku Bessatsu Manual Up Series, pp. 108-115, 1995.

\* cited by examiner the primary cell prepared from an animal organ having a cancer gene or the large T antigen gene in the cell already at the time of the ontogeny. For instance, Japanese Laid-Open Patent Application No. 1993-292958, inventors of which are the present inventors, discloses a method of establishing an immortalized cell line comprising: introducing thermo-sensitive mutant SV40 large T antigen gene into a totipotent cell of a mammal; collecting tissue cells from various organs such as hepatic cells or bone marrow cells of a transgenic animal which was normally born from said mammal; and subculturing the tissue cells. An immortalized cell from an organ of the transgenic mouse introduced with the large T antigen gene of SV40 thermo-sensitive mutant line tsA58 is, especially, said to be very effective in that its proliferation or the expression of differential property can be manipulated by changing temperature (Noble M et al.(1995) Transgenic Research 4, 215-225; Obinata M.(1997) Genes to Cells 2, 235-244).

IMMORTALIZED VASCULAR ADVENTITAL CELL LINE

TECHNICAL FIELD

The present invention relates to an immortalized vascular pericyte line, more particularly to an immortalized vascular pericyte line which can be established through subculturings of brain capillary cells of a transgenic rat introduced with the large T antigen gene of SV40 thermo-sensitive mutant line tsA58, and which expresses PDGF (Platelet-Derived Growth Factor) receptor β and Angiopoietin-1.

PRIOR ARTS

Conventionally, animals have mainly been used in experimental studies for testing safety or effectiveness of pharmaceuticals. However, in order to prevent cruelty to animals, techniques using cultured cells etc. instead of using animals to test and study effectiveness or safety of pharmaceuticals in vitro are now being studied for practical application. For example, animal experiments are carried out after preliminarily experimented by methods using primary cultured cells from living tissues or immortalized cell (established cell) lines that proliferate infinitely. Primary cells, however, proliferate well at the early stage, but their proliferation will gradually come to a halt in the course of repeated subculturings and ends up with death (this event is called cell aging). Further, primary cells are said to alter their properties in the course of subculturings, in addition to the risk that their properties differ each time they are extracted from living tissues. To obtain primary cells sufficient for use in experiments is said to be extremely difficult, especially when the proliferation rate is considerably slow or the cells are micro-organ derived.

Meanwhile, immortalized cells, that are free from cell aging and have acquired ability for infinite proliferation in the course of subculturings of the primary culture, have stable and equal properties. Still, many of such immortalized cells lose part or whole of morphology or function that the cells originally possessed in the organisms, and therefore in the experiments using such immortalized cells, it has been considered difficult to precisely reflect their original properties that the cells displayed in their deriving tissues. Hence, an attempt has been made to transform a primary cell by introducing cancer-causing genes such as ras gene or c-myc gene, E1A gene from adenovirus, the large T antigen gene from SV40 virus, HPV16 gene from Human Papiloma Virus, and the like, to successively maintain the high proliferation ability of the primary cell; and to establish a cell which will not lose its original property even in the course of subculturings. However, to obtain an immortalized cell in its strict definition, i.e. maintaining its original function has been a hard task, because even such an immortalized cell loses some of its function as early as at the preparation of the primary cell and at the introduction of the foregoing cancer genes or large T antigen gene, depending on the tissue used. It has extremely been difficult, especially when preparing and making a cell line using a primary cell with very low speed of proliferation or such deriving from a microorgan.

Meanwhile, a method of establishing an immortalized cell which utilizes a recently established technique to introduce a gene into an individual animal is reported, wherein a transgenic animal which is stably imported with a cancer gene or the large T antigen gene into its chromosome is generated instead of introducing such gene into each cell, and wherein an immortalized cell is established by subcul- Capillary pericytes have been considered with great interest in the studies of vascular wall denatured diseases. Methods using primary cells of capillary pericytes instead of using animals have experimentally been tried in view of preventing cruelty to animals. In doing so, sufficient amount of cells for the experiment use is hard to be obtained from small experimental animals where the numbers of capillary pericytes differ among the tissues, so that tissues of large-sized cattle such as cows or the like should be used. However, information obtained from the cultured cells of large-sized cattle such as cows etc. can hardly be reduced back to the organism, therefore, a capillary pericyte line as an effective alternative have been longed for. The subject of the present invention is to provide an immortalized vascular pericyte line maintaining its original function/property in the tissue from which said cell line derived, a method of establishing said cell line, and a method for screening an effective substance using said cell line.

SUMMARY OF THE INVENTION

The present inventors have made a keen study to solve the above-mentioned problems and have found that when generating a cell line from a microorgan such as brain capillary pericyte, rats with about tenfold weight of mice is advantageously used to prepare cells for establishing an immortalized cell line. According to the finding, the inventors have found that an immortalized capillary pericyte line can be established by the step comprising: producing a transgenic rat introduced with the large T antigen gene of SV40 thermo-sensitive mutant line tsA58 as an immortalized gene; homogenizing the cerebral tissue of said transgenic rat to separate the brain capillary; treating the obtained brain capillary with protease; and subcultivating the obtained cell. The present invention is thus completed.

The present invention relates to an immortalized vascular pericyte line which maintains ability to express PDGF receptor β and Angiopoietin-1, an immortalized vascular pericyte line of claim 1 which derives from a brain capillary pericyte, an immortalized vascular pericyte line of which expresses the large T antigen gene of SV40 thermo-sensitive mutant line tsA58, an immortalized vascular pericyte line, which has ability to deposit calcium on matrix by dense culture, an immortalized vascular pericyte line, which is a rodent-origin, an immortalized vascular pericyte line wherein the rodent is a rat, an immortalized brain capillary pericyte line TR-PCT1 (FERM BP-7024).

The present invention also relates to a producing method of an immortalized vascular pericyte line comprising:

homogenizing the cerebral tissue of a transgenic rat which is introduced with the large T antigen gene of SV40 thermo-sensitive mutant line tsA58; treating the obtained brain capillary with protease; subcultivating said brain capillary cell; and establishing an immortalized cell expressing thermo-sensitive SV 40 large T antigen, PDGF receptor β and Angiopoietin-1, and a producing method of an immortalized vascular pericyte line, wherein the immortalized vascular pericyte line has ability to deposit calcium on matrix by dense culture.

The present invention further relates to a screening method of a promoting agent or an inhibitory substance for the expression of differential property in an immortalized vascular pericyte, wherein the immortalized vascular pericyte line is cultured in the presence of a subject material and the activity and/or the expression level of the marker protein in said cell is measured and evaluated, a screening method of a promoting agent or an inhibitory substance for the expression of differential property in the immortalized vascular pericyte of claim 10, wherein the marker protein is PDGF receptor β, Thy-1, ICAM-1, or Angiopoietin-1, a screening method of a promoting agent or an inhibitory substance for the proliferation in an immortalized vascular pericyte, wherein the immortalized vascular pericyte line is cultured in the presence of a subject material and the proliferation level of said cell is measured and evaluated, and a screening method of a promoting agent or an inhibitory substance for calcium deposition on matrix in an immortalized vascular pericyte, wherein the immortalized vascular pericyte line is dense-cultured in the presence of a subject material and the calcium level deposited on matrix in said cell is detected and evaluated.

The present invention still further relates to a promoting agent for the expression of differential property in the immortalized vascular pericyte obtained by the screening method, a promoting agent for the proliferation in the immortalized vascular pericyte obtained by the screening method, a promoting agent of the calcium deposition on matrix in the immortalized vascular pericyte obtained by the screening method, an inhibitory substance for the expression of differential property in the immortalized vascular pericyte obtained by the screening method, an inhibitory substance for the proliferation in the immortalized vascular pericyte obtained by the screening method, and an inhibitory substance for the calcium deposition on matrix in the immortalized vascular pericyte obtained by the screening method.

THE BEST MODE TO CARRY OUT THE INVENTION

An immortalized vascular pericyte line of the present invention may be any one among established cells that maintain ability to express PDGF receptor β and Angiopoietin-1. The examples include cell lines which derives from the brain capillary pericyte, which expresses the large T antigen gene of SV40 thermo-sensitive mutant line tsA58, and which can deposit calcium on matrix by dense culture. TR-PCT1 line (FERM BP-7024) is a particular example of such immortalized vascular pericyte. An immortalized vascular pericyte line of the present invention can be obtained from rodents such as rats or the like. Among them, rats are preferable for use in preparation of the cell for establishment of a cell line from various organs, especially when generating a line from a microorgan-derived cell such as a brain capillary pericyte due to the easiness to obtain primary cells from rats by separating the organ. The method of producing an immortalized vascular pericyte line will now be explained in the following with examples using rats.

For instance, the cerebral tissue of a transgenic rat introduced with the large T antigen gene of SV40 thermo-sensitive mutant line tsA58 is homogenized to separate brain capillaries. The obtained brain capillaries are treated with protease such as collagenase, after which the brain capillary pericytes are subcultured, which leads to the establishment of the immortalized cells expressing PDGF receptor β which is a surface marker for a perithelial cell and Angiopoietin-1 which is specific for the vascular wall cell.

The transgenic rat introduced with the above-mentioned large T antigen gene of SV40 thermo-sensitive mutant line tsA58 can be produced as described below. For example, total DNA of tsA58 ori (−)-2, where the replication origin (ori) of SV40 is deleted, is digested and opened with the restriction enzyme BamHI and is introduced into pBR322, to obtain plasmid pSVtsA58 (−)-2 (Ohno T.et al., Cytotechnology 7, 165-172, 1991), which is then considerably amplified in *E.Coli* following the usual protocol. These amplified plasmids are then digested with the restriction enzyme BamHI to remove the vector sites, and thus DNA fragment having the large T antigen gene of tsA58 is prepared. When DNA fragment containing the promoting agent of this large T antigen gene is genetically introduced into a totipotent cell of an animal like rodent such as a rat etc. according to an ordinary protocol, a gene-introduced rat, i.e. transgenic rat, can be produced which has the large T antigen gene of SV40 thermo-sensitive mutant line tsA58 in every each of its cells. Every somatic cell of this transgenic rat expresses the large T antigen genes of tsA58. Specific examples of the above totipotent cells include pluripotent ES cells other than fertilized eggs or early embryos. Known methods of gene introduction such as microinjection, electric pulsing, Liposome method, Calcium-Phosphate method, or the like may be exemplified as methods to introduce DNA into totipotent cells.

The large T antigen gene of SV40 thermo-sensitive mutant line tsA58 can be introduced into the ovum by transplanting the nucleus of totipotent cells (cultured cells) of animals like rodents such as rats as mentioned above to an enucleated unfertilized egg for initialization (nuclear transplantation). And it is possible to effectively generate a gene-introduced rat, i.e. a transgenic rat, introduced with the large T antigen gene of tsA58 into the chromosomes of cells of each tissue already at the time of the individual development, as follows: the male pronucleus of pronucleus-stage fertilized egg is microinjected with the large T antigen gene of SV40 thermo-sensitive mutant line tsA58; the resulting ovum is transplanted into oviduct of the recipient rat to gain a newborn rat; baby rats having the injected gene are selected; and as a consequence, individuals carrying such gene are constantly obtained.

With regard to the immortalized vascular pericyte of the present invention, the pellets can be obtained as follows: the cerebrum of the transgenic rat generated as the foregoing is extracted and thoroughly washed in buffer solution; the cerebrum is cut into thin strips that are ground with a homogenizer for slurry; and thus obtained slurry is added buffer solution to be centrifuged. The pellets thus obtained are suspended in the enzymic (protease) solution and enzymically treated as the solution is shaken so that capillaries are separated from the unnecessary tissues for centrifuging again, and the pellets obtained through the centrifugation are suspended in DMEM containing 20% fetal bovine serum. This suspension solution is spread on a culture glass plate and is subjected to two subculturings, and the colonies are formed. The colonies with relatively high speed of proliferation are isolated from the surrounding cells with a penicillin cup and the colonies are formed again. Again, the colonies with relatively high speed of proliferation can be isolated from the peripheral cells with a penicillin cup.

The immortalized vascular pericyte isolated as described above is characteristic in maintaining infinite proliferation ability at 33° C. to 37° C. and in controlling the expression of cell-specific differential property to halt the proliferation at 39° C. Further, the isolated immortalized vascular pericytes can be identified by detecting the expression of thermo-sensitive SV40 large T antigen, PDGF receptor β, and Angiopoietin-1 by RT-PCR and/or Western blotting. Said immortalized vascular pericyte line shows high proliferation activity at 33° C. even after 50 subculturings and still maintains the function of the brain capillary pericyte.

The immortalized vascular pericyte line of the present invention is useful for studying vascular wall denatured diseases, autoimmune diseases originating in the brain, the diseases associated with nutritional metabolism of the brain and with disorder of homeostasis function, neovascularization-involved diseases such as solid tumor, arteriosclerosis, etc., and for studying diagnosis or the development of the therapy for these diseases at the cell level. In addition, the immortalized vascular pericyte line of the present invention maintains expression of various cell markers and the cultivation on the dense glass plate brings about matrix structure with abundant calcium composition. Therefore, as described below, it may be applied in the screening of useful substances such as pharmaceuticals etc. that target vascular pericytes.

The screening method of the present invention includes: a screening method of a promoting agent or an inhibitory substance for the differential property expression in an immortalized vascular pericyte, wherein the above immortalized vascular pericyte line is cultured in the presence of a subject material and the activity and/or the expression level of marker proteins such as PDGF receptor β, Thy-1, ICAM-1, Angiopoietin-1 or the like in said cell is measured/evaluated; a screening method of a promoting agent or an inhibitory substance for proliferation in an immortalized vascular pericyte, wherein the above immortalized vascular pericyte line is cultured in the presence of a subject material and the proliferation level of said cell is measured/evaluated; and a screening method of a promoting agent or an inhibitory substance for calcium deposition on matrix in an immortalized vascular pericyte, wherein the above immortalized vascular pericyte line is dense-cultured in the presence of a subject material and the calcium level deposited on matrix of the cell is detected/evaluated.

The screening of a promoting agent or an inhibitory substance for the differential property expression in the above mentioned immortalized vascular pericyte is carried out by cultivating the immortalized vascular pericyte line in the presence of a subject material of various concentrations respectively, detecting/measuring the level of marker proteins expressed after a certain period of cultivation, and comparing with the control cultured in the absence of a subject material for evaluation. For instance, PDGF receptor β or Thy-1, a surface marker for a vascular pericyte, can be immunochemically detected for measurement by the usual method using a specific antibody for each. In addition, vascular wall-specific Angiopoietin-1 or ICAM-1 is measured by detecting expression of the corresponding mRNA by the usual method. Screening of a promoting agent or a inhibitory substance for proliferation in the above immortalized vascular pericyte is carried out by cultivating the immortalized vascular pericyte line in the presence of a subject material of various concentrations respectively, measuring/analyzing the cell count and cell morphology after a certain period of cultivation, and comparing with the control cultured in the absence of a subject material for evaluation. Further, a promoting agent or an inhibitory substance for calcium deposition on matrix in the above immortalized vascular pericyte is screened by dense culture of the immortalized vascular pericyte line in the presence of a subject material of various concentrations which is followed by, after a certain period of cultivation, detecting calcium deposition on matrix with a microscope etc., and by comparing with the control cultured in the absence of a subject material for evaluation.

Promoting agents or inhibitory substances for differential property expression in the immortalized vascular pericyte, for proliferation in an immortalized vascular pericyte, and for calcium deposition on matrix in the immortalized vascular pericyte, which are obtainable by these screening methods, can be employed and will be useful as a remedy and as a drug for prevention and/or symptom-amelioration for treating patients suffering vascular wall denatured diseases, neovascular diseases, autoimmune diseases of the brain, diseases associated with nutritional metabolism of the brain and with disorder of homeostasis function.

The present invention will now be explained in more detail with examples below, but the scope of the invention will by no means be limited by these examples.

EXAMPLE 1

Production of Transgenic Rats

A transgenic rat introduced with DNA of SV40 thermo-sensitive mutant line tsA58 was produced by the following procedure.

(Preparation of the Gene to Be Introduced)

Genomic DNA of SV40 thermo-sensitive mutant line tsA58 was used for microinjection. DNA to be introduced was prepared following the usual protocol from DNA clone pSVtsA58ori (−)-2 (Ohno T. et al., Cytotechnology, 165-172, 1991; see FIG. 1) in which genomic DNA of tsA58 was digested and opened with restriction enzyme BamHI and was then introduced into BamHI site of pBR322 and in which SfiI sequence is subsequently converted to Sac II to have ori (−) which lacks SV40 replication origin (ori). Briefly, plasmid DNA, pSVtsA58ori(−)-2, obtained by having been considerably amplified within *E.coli* was digested with restriction enzyme BamHI (Takara), and was then separated by agarose gel electrophoresis (1% gel; Boehringer) after which the gel was lysed. Subsequently, DNA was collected by phenol/chloroform treatment and ethanol precipitation. The purified DNA collected was lysed in TE buffer (10 mM Tris-HCl containing 1 mM EDTA; pH7.6) and the solution containing 170 μg/ml purified DNA was obtained. The DNA solution was diluted to 5 μg/ml with injectable buffer (10 mM Tris-HCl containing 0.1 mM EDTA; pH7.6) to prepare the injectable DNA solution. The prepared DNA solution was kept at −20° C. until performing injection.

(Production of Transgenic Rats)

The injectable DNA solution prepared according to the foregoing procedure was microinjected into a rat's fertilized egg at the pronucleus stage as follows. Sexually matured 8-week-old Wister rats were fed under 12-hour bright/dark cycles (bright hours: 4:00-16:00), temperature of 23±2° C., and moisture of 55±5%. Sexual cycles of the female rats were monitored with their vaginal smear and the day to administer hormone was selected. First, the female rats were intraperitoneally injected with 150 IU/kg pregnant mare serum gonadotropin (PMSG) (Nippon Zenyaku; PMS Zenyaku), and 48 hours later with 75 IU/kg human chorionic gonadotropin (hCG) (Sankyo Zoki; Puberogen) to induce superovulation, after which the female rats were co-resided with male rats for intercrossing. Fertilized eggs at the pronucleus stage were collected by oviduct perfusion at 32 hours after the hCG injection. mKRB solution (Toyoda Y. and Chang M. C., J. Reprod. Fertil., 36, 9-22, 1974) was used for oviduct perfusion and egg cultivation. The fertilized eggs collected were enzymically treated for 5 mm. at 37° C. in mKRB solution containing 0.1% Hyaluronidase (Sigma; Hyaluronidase Type 1-S) to remove cumulus oophorus cells, after which the eggs were washed three times in mKRB solution to remove enzyme and were kept in a C02-incubator (5% CO$_2$-95% Air, 37° C., saturated moisture) until DNA injection was conducted. The rat's fertilized eggs, thus obtained, were injected with the above DNA solution in the male pro-nucleus. 228 eggs injected with the DNA solution were transplanted into 9 recipient rats and 80 rats were born. Whether DNA is introduced into the rats by injection was examined by PCR with DNA prepared from tails that are cut off just after weaning [primers used; tsA58-1A, (SEQ ID NO:1) 5'-TCCTAATGTGCAGTCAGGTG-3'(corresponding to the 1365-1384 site), tsA58-1B, (SEQ ID NO:2) 5'-ATGACGAGCTTTGGCACTTG-3' (corresponding to the 157 1-1590 site)]. As a result, transgenic rats from 11 lines (male lines: #07-2, #07-5, #09-6, #12-3, #19-5, female lines: #09-7, #11-6, #12-5, #12-7, #18-5, #19-8), that survived up to 12 weeks when sexually maturing period is over, were obtained from among 20 rats that were confirmed to have been gene-transferred (6 males, 8 females, 6 sex-unknown). These Go-generation transgenic rats and Winster rats were intercrossed and the gene transmission to the next and following generations were confirmed in 2 lines and 3 lines among male founders (#07-2, #07-5) and female founders (#09-7, #11-6, #19-8), respectively.

EXAMPLE 2

Separation of Brain Capillary Pericytes

To separate brain capillary pericyte from a cerebrum, a method was employed which is an improvement of the methods of Ichikawa and others (Ichikawa N et al., (1996) J. Pharmacol. Toxicol. Method., 36, 45-52) and Capetandes and others (Capetandes A and Gerristen ME (1990) Invest. Ophthalmol. Vis. Sci., 31, 1738-1744). The brain of the transgenic rat (single) which was introduced with the large T antigen gene of SV40 thermo-sensitive mutant line tsA58 obtained according to Example 1 was extracted. The extracted brain was removed of diencephalon and brain stem etc. except for the cerebrum, and the cerebrum was then thoroughly washed with the buffer for preparation (122 mM NaCl, 3 mM KCl, 1.4 mM CaCl$_2$, 1.2 mM MgSO$_4$.7H$_2$O, 0.4 mM K$_2$HPO$_4$, 10 mM Glucose, 10 mM Hepes; pH7.4) which was ice-cooled in a clean bench. The tissue of the washed cerebrum was cut into small strips of 1 to 2 mm$^2$ and the strips were transferred to a 10 mL Potter-Elvehjem homogenizer (Tokyo Rikakikai). The sectioned brain was then added the ice-cooled buffer for preparation with the four-fold amount of the brain and was stroked up and down for 10 times for homogenizing the tissue. Then the same amount of PBS containing 32% dextran was added therein and the tissue was stroked up and down for 3 times to obtain the slurry. The pellets obtained by centrifuging the slurry (4° C., 15 min at 4500 g) were suspended in 2.4 mL enzymic solution [PBS containing 0.066% collagenase/dispase (Boehringer Mannheim), 0.033% BSA (Sigma)], followed by enzymic treatment (37° C., 3 h) in order to have unnecessary extracellular matrix separated and the pellets were obtained by centrifugation (4° C., 5 min at 600 g). The pellets thus obtained were dispersed in 10 mL culture solution (DMEM supplemented with 100 U/mL benzylpenicillin potassium, 100 µg/mL streptomycin sulfate, 2.50 µg/mL amphotericin B, 20% FCS) and were seeded onto four 35 mm φ culture grass plates (Falcon). The pellets were cultured (primary culture) in a 33° C. CO$_2$ incubator (5% CO$_2$-95% Air, saturated humidity). The media were replaced twice a week, and subculturings were carried out around every each week with Trypsin solution (0.05% Trypsin, 0.53 mM EDTA; Gibco BRL). After undergoing two subculturings, 10$^4$ cells were seeded onto a 100 mm φ culture plate (Falcon). The media was replaced twice a week. Colonies with relatively high speed of proliferation where colonies were formed on day 7-10 were isolated from the surrounding cells with a penicillin cup. 10$^3$ cells obtained were seeded again onto a 100 mm φ culture plate followed by cultivation in a 33° C. CO$_2$ incubator for colony formation. Two cell lines (TR-PCT1, TR-PCT2) were obtained by isolating colonies with relatively high speed of proliferation from the surrounding cells with a penicillin cup.

This TR-PCT1 line is adopted to National Institute of Bioscience and Human-Technology, Agency of Industrial Science and Technology, METI (1-3, Higashi 1-chome, Tsukuba-city, Ibaragi, 305-8566 Japan) with the adoption No."NIBH FERM BP-7024", under the Budapest Treaty defining international acknowledgement concerning microorganism adoption in the procedure of patent application.

EXAMPLE 3

Confirmation of Large T Antigen Protein

Large T antigen protein of two cell lines obtained according to Example 2 was detected by western blotting (Jikken-igaku bessatsu manual UP series "Bunshi-seibutsugakuteki approach niyoru gann-kenkyu protocol" (A special number of experimental medicine: manual up series, "Protocols for studying cancer by molecular biological approach") pp108-115, Yodosha, 1995). The two cell lines were washed with PBS respectively, solubilized in 1 mL solubilized solution (1% SDS, 10 mM Tris, 1 mM EDTA, 10% glycerin), and heated at 100° C. for 10 min. The cell lines were then centrifuged (10 min at 10000 rpm) to remove the insolubilized fractions and the total protein was quantified by Bradford protein assay (BCA protein assay reagent A, PIERCE, was used). Proteins of 10 µg each were separated by SDS polyacrylamid gel electrophoresis and were transcribed onto a nitrocellulose membrane. Anti-SV40 large T antigen mouse antibody (DP02-C; CALBIOCHEM) as the primary antibody and HRP-labeled anti mouse IgG antibody (Amersham) as the secondary antibody were respectively provided to cause reaction on the nitrocellulose membrane blocked with 3% skim milk solution. Subsequently, the reaction specific for large T antigen was detected by using the Amersham's ECL western blotting detection system (RPN2106M1). The result is shown in Table 1. The result confirmed that the large T antigen protein is present in both cell lines obtained.

TABLE 1

| Cell line | TR-PCT1 | TR-PCT2 |
|---|---|---|
| T antigen | + | + |

EXAMPLE 4

Confirmation of PDGF Receptor β and Thy-1

The cell lines obtained were monolayer-cultured and PDGF receptor β and Thy-1 expressed on the cell membrane were immuno-stained for microscopical detection. The cell line TR-PCT1 obtained according to Example 2 was cultured on the 24 well dish (Falcon) cover glass. The culture solution was removed and the cells were washed with PBS, after which 0.5 mL fixing solution (3.6% paraformaldehyde) was added, left at 4° C. for 20 min, and washed thoroughly with PBS. 0.5 mL of 3% BSA-PBS was then added and left at room temperature for 2 hours for blocking, and the cells were reacted with the primary antibody (anti PDGF receptor β goat antibody; Santacruze, FITC-labeled anti Thy-1 mouse antibody; Pharmingen) at room temperature for 1 hour. After washing five times in 0.1% BSA-PBS, the secondary antibody (FITC-labeled anti goat IgG; Sigma (used only for detection of PDGF receptor β)) was provided to cause reaction at room temperature for 1 hour, then washed five times with 0.1% BSA-PBS. Finally, the labeled cells were sealed with glycerin sealing solution (90% glycerol, 1 mg/mL p-phenylendiamine, 0.01M $Na_2HPO_4$; pH 8.5), and were microscopically observed. The result revealed the expression of the PDGF receptor β and Thy-1 on the cell membrane of the cell line TR-PCT1. In addition, the PDGF receptor β expression was also confirmed by western blotting and RT-PCR. Similar result was obtained for TR-PCT2.

EXAMPLE 5

Confirmation of Angiopoietin-1, Osteopontin, and ICAM-1

The cell lines obtained were monolayer-cultured and Angiopoietin-1, Osteopontin, and ICAM-1 expressed on the cells were detected by RT-PCR. The cell line TR-PCT1 obtained in Example 2 was cultured on a 100 mm φ culture plate (Falcon). The culture solution was removed and the cells were washed with PBS, after which the cells were collected with the cell-scraper (Iwaki) and total RNA was extracted with the RNA extraction reagent (Trizol; Gibco). cDNA was synthesized from 1 μg of the extracted total RNA using reverse transcriptase (Rev Tra Ace: TOYOBO) and its expression was confirmed by PCR (exTaq; Takara). The PCR amplification product was confirmed by electrophoresis using 5% acrylamide gel. As a result, the expression of Angiopoietin-1, Osteopontin, and ICAM-1 was confirmed in the cell line TR-PCT1. TR-PCT2 displayed the similar result.

EXAMPLE 6

Confirmation of Calcium Deposition on Matrix by Dense Culture

The cell lines obtained were monolayer-cultured, and calcium deposited on the matrix was confirmed by vonkossa staining. $10^6$ cell lines of TR-PCT1 obtained in Example 2 were cultured in DMEM on a 100 mm φ culture plate (Falcon) and a 100 mm φ collagen type I-coated culture plate (Iwaki). The culture solution for the 100 mm φ collagen type I-coated culture plate was added 10 mM β-glycerophosphate. On day 3, the culture solution was removed and the cells were washed with PBS, after which 8 mL fixing solution (PBS containing 0.1% glutaraldehyde) was added, and left at room temperature for 15 min. The cells were then washed twice in distilled water. Subsequently, 8 mL of 5% silver nitrate solution (Wako) was added to block light, then the cells were left at room temperature for 30 min, after which time the 5% silver nitrate solution was removed and the cells were washed twice in distilled water. The plate was exposed to light at room temperature for 30 min and was microscopically observed. The result revealed the calcium deposition on the matrix for the cell line TR-PCT1, and the increase in the calcium deposition was confirmed on the collagen-coated culture plate. TR-PCT2 also had the similar result.

INDUSTRIAL APPLICABILITY

The present invention enables to provide an immortalized vascular pericyte line useful for: studies of vascular wall denatured diseases, nutritional metabolism of the brain, neovascularization, and autoimmune diseases originating in the brain; screening of the drugs that target vascular pericytes; diagnosis of the diseases associated with nutritional metabolism of the brain and with disorder of homeostasis function; and a study at a cell-level for development of the therapy for these diseases.

What is claimed:

1. An immortalized brain capillary pericyte cell line TR-PCT1 (FERM BP-7024), which expresses thermo-sensitive SV40 large T antigen, PDGF receptor β, and Angiopoietin-1.

2. A method of screening for a promoting agent or an inhibitory substance for the expression of a differential property in an immortalized vascular pericyte, comprising the steps of culturing the immortalized brain capillary pericyte cell line TR-PCT1 (FERM BP-7024) according to claim 1 in the presence of a subject material; and measuring and evaluating the activity and/or the expression level of a marker protein in said immortalized vascular pericyte line.

3. The method according to claim 2, wherein the marker protein is PDGF receptor β, Thy-1, ICAM-1, or Angiopoietin-1.

4. A method of screening for a promoting agent or an inhibitory substance for the proliferation in an immortalized vascular pericyte, comprising the steps of culturing the immortalized brain capillary pericyte cell line TR-PCT1 (FERM BP-7024) according to claim 1 in the presence of a subject material; and measuring and evaluating the proliferation level of said immortalized vascular pericyte line.

5. A method of screening for a promoting agent or an inhibitory substance for calcium deposition on a matrix in an immortalized vascular pericyte, comprising the steps of dense-culturing the immortalized brain capillary pericyte cell line TR-PCT1 (FERM BP-7024) according to claim 1 in the presence of a subject material; and detecting and evaluating the calcium level deposited on said matrix in said immortalized vascular pericyte line.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tcctaatgtg cagtcaggtg                                              20
```

```
<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
atgacgagct ttggcacttg                                              20
```